United States Patent [19]

Usui

[11] Patent Number: 5,046,479
[45] Date of Patent: Sep. 10, 1991

[54] DISPOSABLE BODY WARMER
[75] Inventor: Akio Usui, Tochigi, Japan
[73] Assignee: Mycoal Warmers Company Limited, Tochigi, Japan
[21] Appl. No.: 439,696
[22] Filed: Nov. 21, 1989
[30] Foreign Application Priority Data Nov. 30, 1988 [JP] Japan .................................. 63-300795

[51] Int. Cl.$^5$ ............................ A61F 7/00; F24J 1/00
[52] U.S. Cl. .................................. 126/204; 126/263; 128/399; 128/403; 604/291
[58] Field of Search ....................... 126/204, 206, 263; 128/399, 402, 403; 206/484; 62/530, 457, 112; 604/113, 291

[56] References Cited

U.S. PATENT DOCUMENTS

| Re. 32,026 | 11/1985 | Yamashita et al. | |
|---|---|---|---|
| 2,573,791 | 11/1951 | Howells | |
| 3,301,250 | 1/1967 | Glasser | |
| 3,976,049 | 8/1976 | Yamashita et al. | |
| 4,268,272 | 5/1981 | Taura | 126/206 X |
| 4,516,564 | 5/1985 | Korso et al. | 126/204 |
| 4,554,193 | 11/1985 | Erickson | |
| 4,756,299 | 7/1988 | Podella | |
| 4,865,012 | 9/1989 | Kelley | 126/204 |

FOREIGN PATENT DOCUMENTS 34735 8/1981 Japan.

OTHER PUBLICATIONS

JP-A-57 207748 3/1983 (Kemitsuku) Abstract.
JP-A-58 092 752 8/1983 (Nihon Paionikusu) Abstract.

Primary Examiner—Larry Jones
Attorney, Agent, or Firm—Frishauf, Holtz, Goodman & Woodward

[57] ABSTRACT

A disposable body warmer comprising a flat bag and in a flat form having a thickness of 2 to 5 mm, comprising a heat generating agent comprising iron powder as a main ingredient and mixed therewith 9 to 11% by weight of a water-retaining agent, 18 to 22% by weight of water, an oxidation promotor and sodium chloride. The flat bag is provided with an air-permeable surface having an air permeability per unit of 5,000 to 10,000 sec/100 cc so as to bring about a reduction in the pressure accompanying oxidative heat generation of the heat generating agent packed in the flat bag. The other surface of the flat bag is provided with a nontransferable self-adhesive layer.

15 Claims, 2 Drawing Sheets (a)

(b)

DISPOSABLE BODY WARMER

BACKGROUND OF THE INVENTION

The present invention relates to a self-adhesive disposable body warmer, and more particularly to a self-adhesive disposable body warmer comprising iron powder as a main ingredient, which can set up and maintain a stable attachment, can keep a stable heat distribution state and further can be comfortably used in direct contact with or in close vicinity to the skin.

A disposable body warmer comprises an air-permeable bag and, accommodated therein, a mixture of metal powder such as iron powder available at a relatively low cost with assistants such as water, activated carbon, wood flour and salt and utilizes an exothermic reaction caused by supplying oxygen (air) thereto. It can be easily used by merely opening a wrapped, hermetically sealed bag, and occupies a major proportion of the body warmers in these days.

However, the above-described disposable body warmer requires the use of an attaching means in order to attach the body warmer to the human body. More precisely, the disposable body warmer is not in a form to be attached to the human body without being put in receptacle of an attaching band or the like, or placed in a pocket provided in underwear. In other words, although the disposable body warmer per se is inexpensive, the attaching means is considerably expensive and the attachment of the body warmer to the attaching means and removal thereof from this means are complicated. Further, even when the body warmer is put in such an attaching means or a pocket and attached to the human body, the position of attachment is limited, which often makes it impossible to attach the disposable body warmer properly to that part of the body where a thermal effect is most required.

As an expedient for eliminating the disadvantage of the conventional ordinary disposable body warmer, a self-adhesive heat generating bag has been proposed in Japanese Utility Model Publication (Y2) No. 34735/1981. This bag comprises a heat generating agent capable of generating heat upon being exposed to oxygen and placed in a flat heat generating bag having one surface permeable to oxygen with the other surface being provided with a nontransferable self-adhesive layer all over the surface or in a pattern form. This bag can be substantially properly applied to any site of the human body or the like and can be applied without use any expensive and special attaching means or pocket.

Although the nontransferable disposable body warmer may be thought to have above-described advantage, studies on the utility of this warmer conducted by the present inventor has revealed that such a body warmer generally stands substantially perpendicular or at a slant at least when applied to the human body and that in order to attain substantially uniform heat generation and heat quantity, the heat generating agent placed in the bag should be basically of a flat form and cannot be packed densely like, e.g., a sausage at a even when the peripheral portion is of a thin layer form. That is, the heat generating agent should be packed in a flat form while leaving a considerable space, which inevitably brings about uneven distribution or agglomeration of this agent in the bag when the body warmer is applied to the human body or the like. The uneven distribution, in turn makes the heat generation of the agent in the bag and the temperature distribution accompanying the heat generation uneven, and the agglomeration results in an unpleasantness to the user and further disturbs the state of heat generation.

Specifically, in one part of the heat generating agent, heat generation begins and is completed in an early stage, while in the other part thereof, remarkable heat generation occurs, thus causing skin burns or the like. The agglomerated heat generating agent deteriorates the touch, particularly results in an unpleasantness in a state when directly applied to the skin or applied to the skin through underwear, and remarkably disturbs the state of heat generation because the amount of supply of oxygen is lowered.

SUMMARY OF THE INVENTION

An object of the present invention is to provide a self-adhesive adhesive disposable body warmer comprising iron powder as a main ingredient which can set up and maintain a stable attachment, can keep a stable heat distribution state and further can be comfortably used in direct contact with or in close vicinity to the skin.

The above-described object of the present invention can be attained by a disposable body warmer wherein the air permeability per unit time in an air-permeable surface of a flat bag is limited to 5000 to 10000 sec/100 cc so as to bring about a reduction in the pressure accompanying oxidative heat generation of a heat generating agent packed in said flat bag, said heat generating agent comprises iron powder as a main ingredient and, mixed therewith, 9 to 11% by weight of a water-retaining agent, 18 to 22% by weight of water, a heat generation promoter and salt and packed in a flat form having a thickness of 2 to 5 mm in said flat bag, and nontransferable self-adhesive layer is attached to said flat bag.

The nontransferable self-adhesive layer attached to the flat bag enables the body warmer to be attached to an arbitrary position of the human body or clothing, particularly underwear and further hardly causes the above-described self-adhesive to remain and stain the body or clothing when the body warmer is peeled off.

An intended exothermic reaction can be achieved at a relatively low cost by packing into the above-described flat bag a heat generating agent comprising iron powder as a main ingredient and reaction assistants incorporated therein.

The limitation of the air permeability of the air-permeable surface of the flat bag to 5000 sec/100 cc or less causes the oxidative heat generation of the heat generating agent mainly composed of iron powder placed in the bag to reduce the pressure within the bag. That is, the amount of supply of oxygen (amount of air) is limited to a value less than that necessary for oxidation of that agent so that the above-described flat bag can be maintained in a compression-flattened state under atmospheric pressure during the oxidative heat generation. This compression-flattened flat bag prevents the uneven distribution of the heat generating agent within the bag and equalizes the temperature distribution.

The incorporation of 9% by weight or more of a water-retaining agent, such as wood flour or vermiculite, in a heat generating agent mainly composed of iron powder prevents occurrence of shrinkage during the oxidative heat generation, which contributes to prevention of caking of this agent attributable to the shrinkage. Further, limitation of the maximum amount of the water-retaining agent to 11% by weight enables the amount of the iron powder as the main ingredient and the amount of incorporation of the heat generation promotor and the salt to be properly adjusted, so that it is possible to attain heat generation of the agent as a whole suitable for a body warmer.

Limitation of the amount of water to 18% by weight or more enables an exothermic reaction utilizing iron powder to properly proceed. On the other hand, limitation of the maximum amount thereof to 22% by weight enables set up of a proper heat generation state upon opening of the bag for use, i.e., enables excellent initiation of the heat generation. This prevents the heat generating agent from being unevenly distributed by virtue of proper reduction in the pressure within the bag from the initiation of use of the body warmer and brings about a favorable thermal effect.

The above-described prevention of shrinkage during the oxidative heat generation and improvement in the initiation of the heat generation enables the body warmer to be comfortably used in direct contact with or in close vicinity to the skin.

Limitation of the thickness of the heat generating agent packed in the above-described flat bag to 2 mm or more contributes to the set up of a heat generation state or temperature distrubution favorable for warming the human body or the like, while limitation of the maximum thickness thereof to 5 mm or less restricts the load per unit area of the agent mainly composed of iron powder to thereby aid the prevention of uneven distribution of the agent.

The above-described characteristic features of the present invention enables the heat generating agent mainly composed of iron powder to be maintained in a flat and homogeneous state and makes the agent less susceptible to formation of a agglomerated portion, so that it is possible to surely realize useful and stable warming of the human body or the like in a self-adhesion system.

DETAILED DESCRIPTION OF THE PREFERRED EMBODIMENTS

Figure 1:
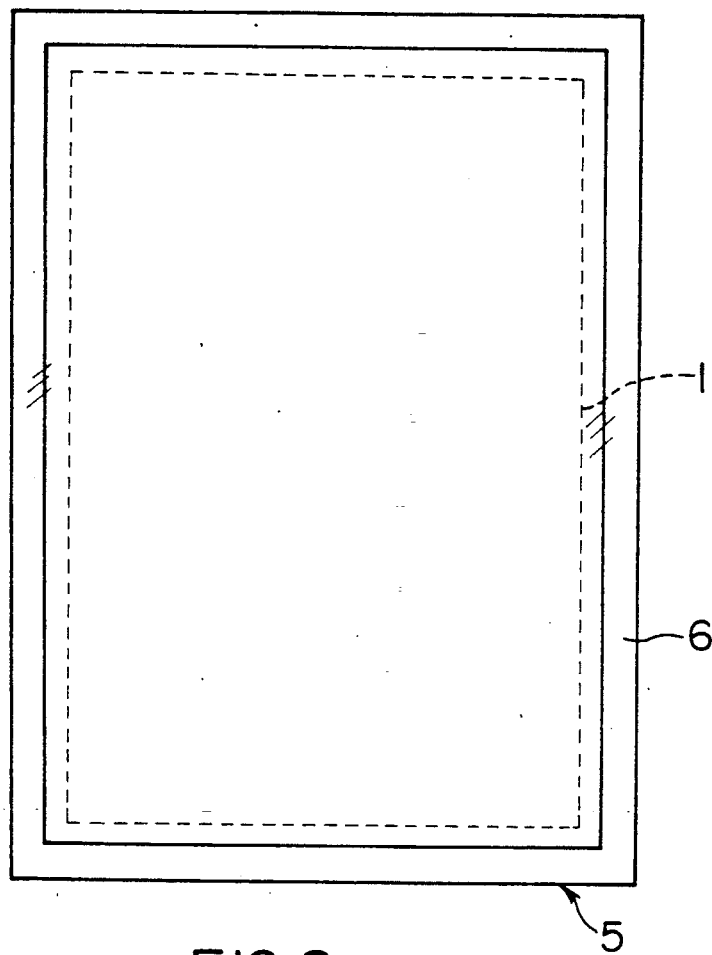
FIG. 1 is a partially cutaway plan view of a disposable body warmer according to the present invention.
Figure 2:
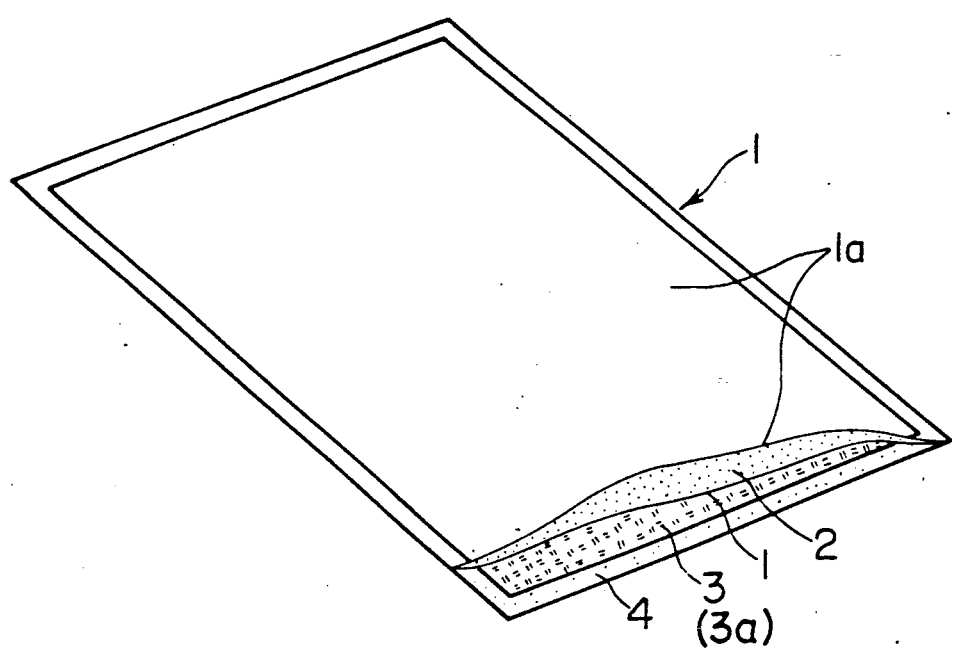
FIG. 2 is a partially cutaway bottom plan view of the disposable body warmer shown in FIG. 1.
Figure 3:
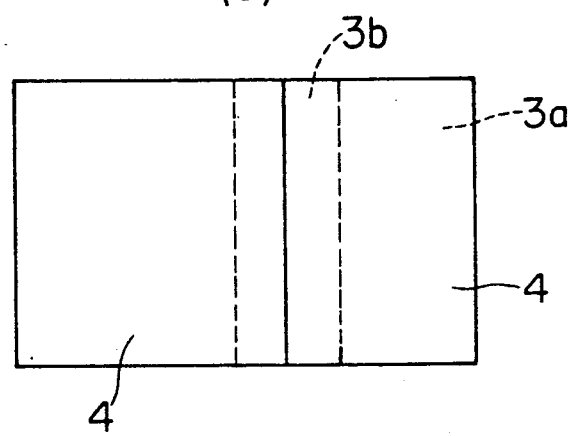
FIG. 3(a) is a plan view of a disposable body warmer according to the present invention having a slit on a release paper.
FIG. 3(b) is a view depicting the manner of releasing said release paper of FIG. 3(a).
Figure 3:
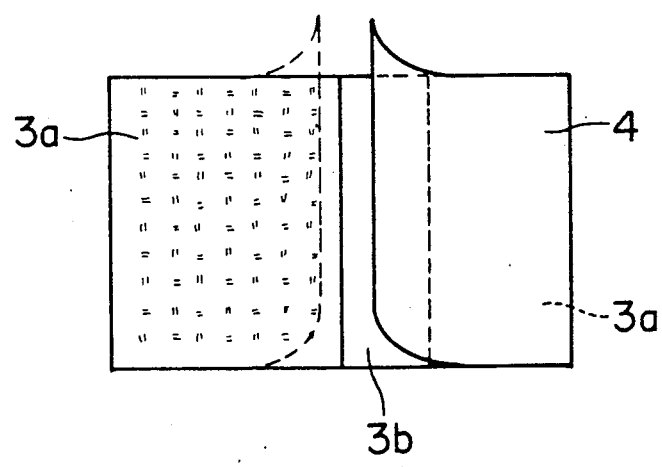

Embodiments of the above-described disposable body warmer according to the present invention will now be described with reference to the accompanying drawings. In a flat bag 1 preferably having one air-permeable surface 1a, the air permeability per unit time of the air-permeable surface is limited to a value less than that of oxygen (the amount of oxygen in the air) necessary for oxidation of a heat generating agent 2 packed in the bag 1 in such a manner as will be described later so that the pressure within the bag is reduced by oxidative heat generation of the agent 2, and further a nontransferable self-adhesive layer 3(a) is attached as an adherend to the other surface of the flat bag. Then, the above-described heat generating agent 2 comprising, as is well-known, iron powder and reaction assistants incorporated therein is packed in a substantially uniform flat form having a thickness of 2 to 5 mm within the bag 1, and the periphery of the bag is sealed.

In the resulting flat bag 1, for commercialization, release paper 4 is adhered to the self-adhesive layer 3(a) and the bag is put in a known air-impermeable packaging bag 5, whereupon hermetic sealing 6 of periphery of the packaging bag is conducted. The degree of the pressure reduction in the oxidative heat generation of the agent 2 in the bag 1 is properly selected taking into consideration the mass of the packed agent 2. It has been experimentally confirmed that use of the bag 1 having an air permeability of 5000 to 10000 sec/100 cc (JIS P8117) enables a proper negative pressure state to be set up. Further, as described above, a lowering of the water content to 22% by weight or less from that of a usual body warmer, i.e., 24 to 25% by weight, enables the bag 1 to be always compression-flattened at atmospheric pressure under conditions of initiation of the heat generation of the agent from an early stage of the heat generation, so that the movement or uneven distribution of the agent 2 in the bag can be effectively prevented. It is apparent that the above-described air permeability is much smaller than that of the bag used in the ordinary body warmer, i.e., 3 to 10 sec/100 cc.

The heat generating agent 2 is a known one comprising iron powder as a main ingredient and, incorporated therein, water, a water-retaining material (charcoal, vermiculite or the like), an oxidation promoter such as activated carbon, and salt. More particularly, the agent 2 comprises about 55 to 65% by weight of iron powder, 18 to 22% by weight of water, 9 to 11% by weight of a water-retaining agent, 3.5 to 4.5% by weight of activated carbon, and about 4.5 to 6% by weight of salt, and the temperature of heat generation accompanying oxidation is adjusted in such a manner that the maximum temperature is 65° C., preferably 62° to 63° C., and the average temperature is 50° to 55° C. Sodium chloride is the preferred salt because of its low price and suitability. Also, it is generally recognized as being safe. In the above-described mixing, as described above, the amount of water is smaller than that of the ordinary body warmer, while the amount of the water-retaining agent is slightly larger than that of the ordinary body warmer, i.e., 7 to 8% by weight.

Although the flat bag 1 may have any size, it is generally prepared so as to have an area of 10×5 cm or more and 20×15 cm or less taking into consideration the convenience in use. It is preferred that the bag 1 be well compatible with the human body or underwear. Examples of the flat bag include flexible thermoplastic sheets and films of polyurethane, polypropylene and polyethylene, and plastic and rubber materials prepared by modification thereof, and non-woven fabric may also be used. The air permeability of the air-permeable surface 1a of the bag 1 is restricted to the above value by a method wherein a sheet or film having interconnected micropores is used as the above-described sheet or film and subjected to a suitable heat fusion treatment for restriction of the permeability. For example, a properly heated hot-fusing agent is homogeneously dispersed in or applied all over the above-described sheet or film having uniform interconnected pores having a diameter of 1 to 50 μm to restrict the air permeability.

Alternatively, it is also possible to properly restrict the air permeability and, at the same time, to obtain a flexible air-permeable surface 1a through lamination of a resin film having interconnected micropores on a known non-woven fabric.

The surface on which the nontransferable self-adhesive layer 3(a) is provided may be essentially impermeable to air because air permeation is hindered by the layer 3 itself. However, in order to ensure the flexibility, the above-described flexible sheet or nonwoven fabric is used as the material, and the self-adhesive layer 3(a) is attached thereto.

The nontransferable self-adhesive layer 3(a) is one prepared by using an organic solvent type or water-base rubber, acrylic or vinyl acetate self-adhesive and introducing a reactive functional group thereinto to enhance the internal cohesive force. For example, an acrylic monomer having 1 to 10% by weight of a functional monomer introduced thereinto may be used as the nontransferable self-adhesive layer. A compound represented by the following general formula (I) is added as the above-described functional monomer in an amount of 1 to 4% by weight:

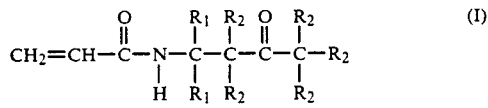

wherein $R_1$ is a lower alkyl group having 1 to 4 carbon atoms and $R_2$ is hydrogen atom or a methylol group.

Alternatively, a compound represented by the following general formula (II) may be added in an amount of 6 to 10% by weight and an acid catalyst may be then added:

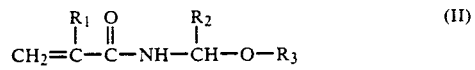

wherein $R_1$ is a hydrogen atom or methyl group, $R_2$ is a hydrogen atom, an alkyl group having 1 to 6 carbon atoms and $R_3$ is an alkyl group having 1 to 18 carbon atoms.

Further, 1 to 8% by weight of a functional monomer represented by the following general formula (III) may be added, and 1 to 5% by weight (in terms of outer percentage) of a water-soluble or dispersive epoxy compound may be then added. All of these nontransferable self-adhesives are known.

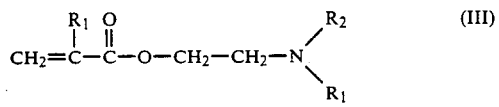

wherein $R_1$ is a hydrogen atom or methyl group and $R_2$ and $R_3$ are each a hydrogen atom or an alkyl group having 1 to 4 carbon atoms.

In the disposable body warmer of the present invention wherein, as described above, the pressure within a flat bag 1 is reduced by oxidative heat generation of a heat generating agent 2, it is preferred that, after opening an air-impermeable packaging bag 5 to take out the flat bag 1 hermetically sealed therein, the flat bag be allowed to stand in the air for a short period of time to initiate the oxidative heat generation before application. As soon as the flat bag is allowed to stand in the air, the oxidative heat generation begins and the pressure within the bag 1 is properly reduced from the initiation of the heat generation because, as described above, the water content is small, thereby properly preventing the agent 2 from being moved or unevenly distributed. 15 seconds to several minutes, particularly about 20 seconds to 1 minutes is sufficient as a time for allowing the flat bag to stand in the air. This period of time does not constute a hindrance to the application of the body warmer when an amount of time for removing release paper 4 adhered to the self-adhesive layer 3 is taken into consideration.

Specific Preparation Examples according to the present invention will now be described.

PREPARATION EXAMPLE 1

35 g of a heat generating agent 2 comprising a mixture of 60% by weight of iron powder with 20% by weight of water, 5.5% by weight of wood flour, 5% by weight of vermiculite, 4.5% by weight of activated carbon and 5% by weight of salt was packed in a 2 to 5 mm thick flat from into a flat bag 1 having a size of 13.5 cm × 10 cm.

One surface of the bag 1 was used as an air-permeable surface 1a, and 30 to 40 g/cm of a nylon spun bond was hot-fused with a heated roll to a 70 μm-thick polyethylene sheet having interconnected micropores through 30 μm-thick porus polyethylene modified so as to enable low temperature adhesion, thus restricting the air permeability to about 8000 sec/100 cc. Meanwhile, a nontransferable self-adhesive layer 3(a) comprising a resin emulsion prepared by mixing 98 parts by weight of an acrylic monomer with 2 parts by weight of a functional monomer was formed on the other surface of the bag 1, and release paper 4 was adhered thereto. The resultant body warmer was put in an air-impermeable polyethylene packaging bag 5 having a size of 12.5 × 17 cm and hermetically sealed, thereby preparing a product.

PREPARATION EXAMPLE 2

A body warmer was prepared in the same manner as that of Preparation Example 1, except that a resin film having an air permeability restricted to about 6000 sec/100 cc under atmospheric pressure was laminated on a nonwoven fabric to form an air-permeable surface of a flat bag for a heat generating agent, and the body warmer thus prepared was put in an air-impermeable packaging bag to prepare a product.

Each product prepared in the above Preparation Examples was unsealed, and each body warmer was adhered to underwear worn on the human body to examine the state of heat generation on 10 samples for each product. The results are shown in the following table.

|  | Max. temp. | Average temp. | Duration |
| --- | --- | --- | --- |
| Product of Prep. Ex. 1 | 55–58° C. | 48–52° C. | 18–20 hr |
| Product of Prep. Ex. 2 | 60–63° C. | 51–53° C. | 14–16 hr |

It has been confirmed that all samples exhibit favorable heat generation as a disposable body warmer and can be stably applied without causing uneven distribution of the agent in the bag during use. It is a matter of course that staining of the underwear by the adhesive scarcely occured when each sample was removed from the underwear after application.

PREPARATION EXAMPLE 3

A body warmer was prepared in the same manner as that of Preparation Example 1, except that a heat generating agent 2 comprising a mixture of 58% by weight of iron powder with 21% by weight of water, 5% by weight of vermiculity, 6% by weight of wood flour, 5% by weight of activated carbon and 5% by weight of salt was used, and the body warmer thus prepared was put in on air-impermeable packaging bag to prepare a product.

This body warmer is one used in direct contact with the skin of the human body. The state of heat generation was examined for 10 samples of the body warmer. As result, it has been found that the average temperature and the duration were 38° to 41° C. and 20 to 24 hr, respectively.

PREPARATION EXAMPLE 4

A body warmer was prepared in the same manner as that of Preparation Example 1, except that a release paper 4 (4) was separated by a slit at the middle portion, and the adhesive surface 3 was having a non-adhesive portion 3b under said slit which was separating the self-adhesive layer 3a (3a) to easily release the release paper 4.

Each product prepared in the above Preparation Example 4 was tested in its adhesion ability through changing area proportion of non-adhesive portion 3b. The results has been that when the area proportion of non-adhesive portion 3b was less than about 30%, the adhesion ability of the product was sufficient. When the non-adhesive portion 3b was made just the center part of the adhesive surface 3, some of the products having 40% non-adhesive portion had enough adhesion ability.

As is apparent from the foregoing description, the disposable body warmer according to the present invention can be properly applied in a self-adhesive system, hardly causes uneven distribution of the heat generating agent even when it is applied to the human body or underwear in a vertical or inclined state, surely exhibits a thermal effect through stable and substantially even temperature distribution, can be properly attached to any site of the human body or the like without use of any special attaching means, can be used with comfort, because it can prevent the heat generating agent from being agglomerated and can smoothly achieve simple use as opposed to the conventional disposable body warmer, which renders the present invention very useful from a commercial viewpoint.

What is claimed is:

1. A disposable body warmer comprising a flat bag having an air-permeable first surface having an air permeability per unit time of 5,000 to 10,000 sec/100 cc so as to bring about a reduction in the pressure accompanying oxidative heat generation of a heat generating agent packed in said flag bag, said heat generating agent comprising iron powder as a main ingredient and, mixed therewith, 9 to 11% by weight of a water-retaining agent, 18 to 22% by weight of water, an oxidation promoter and sodium chloride and being packed in a flat form having a thickness of 2 to 5 mm in said flat bag, and a nontransferable self-adhesive layer being attached to a second surface of said flat bag.

2. The disposable body warmer according to claim 1, which is disposed in an air-impermeable packing bag after a release paper is adhered to said nontransferable self-adhesive layer.

3. The disposable body warmer according to claim 2, wherein said nontransferable self-adhesive layer is adhered to said flat bag after said flat bag containing said heat generating agent is taken out of said air-impermeable packaging bag and pressure within said flat bag is reduced due to initiation of an exothermic reaction.

4. The disposable body warmer according to claim 1, wherein the bag is fabricated from a sheet having interconnected micropores and the air permeability of the air permeability of the air-permeable first surface of said flat bag for containing said heat generating agent is restricted by subjecting said sheet having interconnected micropores to a heat fusion treatment.

5. The disposable body warmer according to claim 4, wherein said sheet having interconnected micropores is a thermoplastic sheet or film of polyurethane, polypropylene or polyethylene, or a plastic or rubber material prepared by the modification thereof.

6. The disposable body warmer according to claim 1, wherein the bag is fabricated from a non-woven fabric and the air permeability of the air-permeable surface of said flat bag for containing said heat generating agent is restricted by laminating a resin film having air-permeable pores on said nonwoven fabric.

7. The disposable body warmer according to claim 1, wherein said nontransferable self-adhesive layer comprises a self-adhesive which hardly remains on the human body or clothes even when released therefrom after application thereto, and is less susceptible to variation of tackiness accompanying said heat generation.

8. The disposable body warmer according to claim 7, wherein said nontransferable self-adhesive has an internal cohesive force enhanced by introducing a reactive functional group into an organic solvent type or water-base rubber, acrylic or vinylacetate self-adhesive.

9. The disposable body warmer according to claim 8, wherein the nontransferable self-adhesive layer comprises 1 to 4 weight % of a compound of the formula

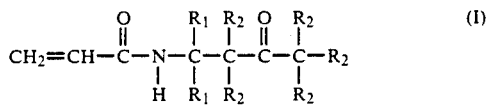

wherein $R_1$ is a lower alkyl group having 1 to 4 carbon atoms and $R_2$ is a hydrogen atom or a methylol group.

10. The disposable body warmer according to claim 8, wherein the nontransferable self-adhesive layer comprises 6 to 10 weight % of a compound of the formula

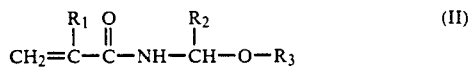

wherein $R_1$ is a hydrogen atom or a methyl group, $R_2$ is a hydrogen atom or an alkyl group having 1 to 6 carbon atoms and $R_3$ is an alkyl group having 1 to 18 carbon atoms.

11. The disposable body warmer according to claim 1, wherein said nontransferable self-adhesive layer is separated by a non-adhesive portion.

12. The disposable body warmer according to claim 11, wherein said non-adhesive portion has an area less than 30% in proportion to an adhesive-containing surface of said flat bag.

13. The disposable body warmer according to claim 1, wherein the water-retaining agent is selected from the group consisting of wood fluor, charcoal, vermmiculite and mixtures thereof.

14. The disposable body warmer according to claim 1, wherein the oxidation promoter is activated carbon.

15. The disposable body warmer according to claim 14, wherein the heat generating agent comprises 55 to 65 weight % of said iron powder, 18 to 22 weight % of said water, 9 to 11 weight % of said water retaining agent, 3.5 to 4.5 weight % of said activated carbon and 4.5 to 6 weight % said sodium chloride.

* * * * *